United States Patent [19]

Steckler et al.

[11] 4,049,608

[45] Sept. 20, 1977

[54] FUNCTIONAL MONOMERS AND COPOLYMERS THEREOF

[75] Inventors: Robert Steckler, Crofton; Fred Robinson, Columbia; Robert F. Farmer, III, Gaithersburg, all of Md.

[73] Assignee: Alcolac Inc., Baltimore, Md.

[21] Appl. No.: 706,206

[22] Filed: July 19, 1976

Related U.S. Application Data

[62] Division of Ser. No. 498,090, Aug. 16, 1974, abandoned.

[51] Int. Cl.$^2$ ............................................. C08L 33/14
[52] U.S. Cl. ........................ 260/29.6 SQ; 260/29.6 H
[58] Field of Search ............... 260/29.6 SQ, 29.6 H, 260/79.3 MU

[56] References Cited

U.S. PATENT DOCUMENTS

| | | | |
|---|---|---|---|
| 2,923,734 | 2/1960 | Sheetz | 260/29.6 SQ |
| 3,306,871 | 2/1967 | Miller | 260/29.6 SQ |
| 3,551,479 | 12/1970 | Emmons | 260/79.3 MU |
| 3,907,870 | 9/1975 | Kozuka et al. | 260/29.6 SQ |

*Primary Examiner*—M. J. Welsh
*Assistant Examiner*—Regenia F. Hughes
*Attorney, Agent, or Firm*—George L. Tone

[57] ABSTRACT

Novel copolymerizable esters of cinnamic acid or an ω-alkenoic acid of from 4 to 18 carbon atoms, such as undecylenic acid, with certain hydroxyalkane sulfonic acids, such as isethionic acid, are described together with processes of making them and copolymers thereof. These novel copolymerizable esters may be made by reaction of the ω-alkenoic or cinnamic acid with the hydroxyalkane sulfonic acid or a sultone, such as propane sultone. These novel ester are useful as copolymerizable surfactants in the emulsion polymerization of ethylenically unsaturated monomers; particularly for the production of self-stabilizing latices of polymeric materials possessing excellent mechanical stability and from which can be deposited films having improved adhesion, pigment wetting and bonding properties and greatly improved resistance to water. They are also useful as comonomers for the production of polymeric materials having sulfonic acid functionality, such as polyelectrolyte materials based on acrylonitrile, vinyl chloride, vinyl acetate, acrylates, methacrylates, styrene, etc.; for example, when used as a comonomer in the production of fibers and films based on the above monomers, they impart improved dye receptivity and anti-static properties to the polymeric fibers and films so made.

4 Claims, No Drawings

FUNCTIONAL MONOMERS AND COPOLYMERS THEREOF

This is a division, of application Ser. No. 498,090 filed Aug. 16, 1974 and now abandoned.

The present invention relates to a new class of esters of an alkenoic acid selected from the group consisting of cinnamic acid and ω-alkenoic acids of from 4 to about 18 carbon atoms with a hydroxyalkane sulfonic acid of from 2 to about 6 carbon atoms. These novel esters are useful as comonomers with vinyl and other ethylenically unsaturated monomers for the production of copolymeric materials having sulfonic acid functionality and are especially useful as copolymerizable sufactants and emulsifiers, in the emulsion polymerization of vinyl and other ethylenically unsaturated monomers.

BACKGROUND OF THE INVENTION

A number of polymerizable esters of unsaturated acids of relatively low molecular weight, particularly those of alphamethylene carboxylic acids, e.g. acrylic and methacrylic acid, with hydroxyalkane sulfonic acids have been described in the art, see for example U.S. Pat. No. 3,024,221 issued Mar. 6, 1962 to Le Fevre and Sheetz and U.S. Pat. No. 3,679,737 issued July 25, 1972 to Pohlemann and Wurmb and have found use as comonomers in the polymerization of vinyl and other ethylenically unsaturated monomers, including use as copolymerizable surfactants, emulsifiers, (usually in admixture with other more conventional emulsifiers, such as sodium lauryl sulfate) in emulsion polymerizations. One disadvantage of the use of these known polymerizable esters as a comonomer is that they substantially increase the water susceptibility of the resulting polymers and thus adversely effect the properties of the polymers for many applications.

SUMMARY OF THE INVENTION

We have now found that esters of an alkenoic acid selected from the group consisting of cinnamic acid and ω-alkenoic acids of from 4 to about 18 carbon atoms with a hydroxyalkane sulfonic acid of from 2 to about 6 carbon atoms, while not readily homopolymerizable under ordinary conditions, are copolymerizable with vinyl and other ethylenically unsaturated monomers to yield polymeric products having new and useful properties. They are also copolymerizable surfactants having good emulsifying properties and thus are especially adapted for use in the emulsion polymerization of vinyl and other ethylenically unsaturated monomers, where they serve the dual function of emulsifier and comonomer.

The novel cinnamic esters of this invention can be represented by the following general formula:

Formula 1.

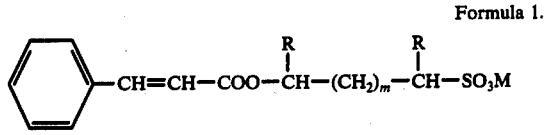

and the novel esters of ω-alkenoic acids of from 4 to about 18 carbon atoms may be represented by the following general formula:

Formula 2.

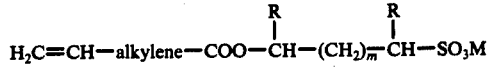

wherein:
the alkylene group may be either straight or branch chained, and contains from 1 to about 15 carbon atoms;
R represents a member of the group consisting of hydrogen and lower alkyl, e.g. methyl and ethyl;
M represents a cation selected from the group consisting of hydrogen, alkali metal (e.g. sodium, potassium, lithium, etc.), alkaline earth metal (e.g. calcium, magnesium, strontium, etc.), ammonium and amino; and
m represents an integer of from 0 to 4, provided however that the total number of carbon atoms in the group

is from 2 to about 6.

The forgoing esters may be made by condensing one mole of an alkenoic acid (either cinnamic acid or an ω-alkenoic acid of from 4 to about 18 carbon atoms) with one mole of either (a) a hydroxyalkane sulfonic acid of from 2 to about 6 carbon atoms or (b) an alkane sultone, preferably containing from 3 to about 6 carbon atoms. Specific and preferred reaction conditions are described in greater detail below. It is a principal object of this invention to provide a new class of copolymerizable monomers and methods for their preparation.

A further object of the invention is to provide an improved process, utilizing the copolymerizable monomers of this invention, of emulsion polymerization; and further to provide improved copolymers obtained by such process.

Other and further objects will be apparent as the present description progresses.

DETAILED DESCRIPTION OF THE INVENTION

In general the esterification, when using hydroxyalkane sulfonic acids, is effected by heating the reactants, either in the presence or absence of inert solvents and in the presence or absence of a catalyst, to a temperature of from slightly lower than 100° C. to 200° C. or somewhat higher, until the desired degree of esterification of the alkenoic acid, preferably at least about 80% esterification, of the alkenoic acid has been effected. The reactants are preferably employed in about equimolar proportions but some excess, say 10–20% or more excess, of either reactant may be employed if desired.

The preferred alkenoic acids for making the novel esters of the present invention are cinnamic acid and undecylenic acid; but other ω-alkenoic acids of 4 to about 18 carbon atoms may be used if desired; as examples thereof may be mentioned: vinylacetic acid, allylacetic acid, 2-methyl-5-pentenoic acid, 5-hexenoic acid, 7-octenoic acid, 9-decenoic acid, undecylenic acid (10-undecenoic acid), 11-dodecenoic acid, 12-tridecenoic acid, 14-pentadecenoic acid, 4-methyl-14-pentadecenoic acid, 2-methyl-16-heptadecenoic acid, 17-octadecenoic acid, and the like.

As examples of hydroxyalkane sulfonic acids which may be used may be mentioned isethionic acid (2- hydroxy-1-ethane sulfonic acid), 2-hydroxy-1-propanesulfonic acid, 1-hydroxy-2-propanesulfonic acid, 2-hydroxy-1-butanesulfonic acid, 1-hydroxy-2-butanesulfonic acid, 3-hydroxy-2-butane sulfonic acid, 1-hydroxy-2-methyl-2-propanesulfonic acid, 2-hydroxy-2-methyl-1-propanesulfonic acid, 2-hydroxy-2-phenylethanesulfonic acid, 3-hydroxy-1-propanesulfonic acid, 3-hydroxy-1-butane sulfonic acid, 4-hydroxy-1-butanesulfonic acid, and the like. These hydroxyalkanesulfonic acids may be used either in the form of the free acid or in the form of their salts, preferably their alkali metal (e.g. sodium) salts.

Particularly when the hydroxyalkanesulfonic acids are used in the form of their salts (such as sodium isethionate) the reaction rate and yields of the desired esters can be greatly improved by effecting the esterification in the presence of a catalyst. We particularly prefer aluminum sulfate $(Al_2SO_4)_3 \cdot 14H_2O$ or zirconium sulfate $(Zr(SO_4)_2 \cdot 4H_2O)$, in amounts ranging from 0.05–5% by weight of the reaction mixture, as the catalyst. Other suitable catalysts include (in amounts of from 0.05–5% by weight of the reaction mixture:

| Hypophosphorous acid | $(H_3PO_2)$ |
| --- | --- |
| Phosphorous acid | $(H_3PO_3)$ |
| Boric acid | $B(OH)_3$ |
| Aluminum chloride | $(AlCl_3)$ |
| Stannous chloride | $(SnCl_2)$ |

Other catalysts are known in the art and may be used, if desired.

As examples of suitable sultones may be mentioned:
1,3-propanesultone
1,4-butanesultone
1,3-butanesultone
1,3-pentanesultone
1,4-pentanesultone
1,4-hexanesultone and
1,6-hexanesultone.

The esterification of the alkenoic acid with a sultone, is preferably carried by reacting a salt of the alkenoic acid, such as an alkali metal salt (e.g. the sodium salt thereof) of the alkenoic acid with an equimolar amount of the sultone, although an excess of up to twice of the sultone may be used. The reaction is advantageously carried out in an inert solvent and satisfactory results have been obtained when methanol was employed as the solvent; however, other lower alkanols of up to 6 carbons; e.g. ethanol, propanol, n-butanol, isobutanol, tert.-butanol, n-hexanol and cyclohexanol, can be used. These alkanols are normally used in an amount of from 3 to 12 moles of alkanol per mole of alkenoic acid. Temperatures in the range of from about 40° C. to about 60° C. ordinarily are used although somewhat lower or higher temperatures may be used. The novel copolymerizable esters of the present invention are, as previously stated, especially useful as copolymerizable surfactants and internal stabilizers in the emulsion polymerization of vinyl and other ethylenically unsaturated monomers. In this use they have a number of advantages over the esters of alpha methylene carboxylates of hydroxyalkane sulfonic acids which have been reported in the prior art. Among these advantages are the following:

1. Our novel esters do not homopolymerize under the usual reaction conditions used in commercial emulsion polymerizations.

2. The alpha-methylene carboxylates as a class, including those of hydroxyalkane sulfonic acids, are susceptible to numerous chemical reactions (e.g. Michael addition) owing to the proximity of the double bond and the carboxyl functionality. These reactions do not occur under normal conditions of use with our novel esters; thereby broadening the conditions of use of our products.

3. Small particle size emulsions (latices) may be routinely made without requiring the addition of other surfactants.

4. In the art of emulsion polymerization it is frequently useful to add pre-emulsified monomers during the course of polymerization. This practice often being advantageous in exercising control over the reacting system, particularly with monomers that produce considerable heat during reaction. The novel esters of this invention offer the advantage of being useful in this technique without requiring the use of other, additional surfactants. Moreover, when it is advantageous to use a low molecular weight copolymerizable surfactant in a particular polymerization, small amounts of the novel esters of this invention may be used to prepare the pre-emulsion, without diluting the effect desired from the low molecular weight copolymerizable surfactant, with the result that essentially no free surfactant need exist in the final polymerization product. This unique advantage can be obtained in emulsion polymerizations using any of the known types of lower molecular weight copolymerizable surfactants as latex stabilizers, including the alpha methylene carboxylates mentioned above.

5. It has long been an objective to produce aqueous polymer systems having good water resistance for use in many coating applications. Traditionally, solvent based polymers have been used for this application. The use of polymers made by aqueous based (emulsion) systems was discouraged because the surfactants required in these systems were deleterious to the end use properties of the polymers so obtained. We have found that when the novel esters of this invention are used in the preparation of otherwise conventional emulsion polymerization systems, the resulting polymeric latices yield polymer films having enhanced water resistance.

The novel esters of the present invention are useful as comonomers in the polymerization of all types of polymerizable vinyl and other ethylenically unsaturated monomers, including mixtures of such monomers. As examples of the polymerizable monomers that can be copolymerized with the copolymerizable esters of the present invention may be mentioned: ethylene, the styrene compounds, ethylenically unsaturated acids and derivatives such as the acrylic and methacrylic acids and salts, acrylic and methacrylic esters, acrylic and methacrylic nitriles, acrylic and methacrylic amides, acrylic and methacrylic anhydrides, maleic esters, maleic anhydride, maleic acid polyesters, unsaturated alcohol esters, unsaturated ketones, and other compounds containing one or more ethylenic linkages capable of addition polymerization. Specific examples of such ethylenically unsaturated compounds are ethylene, styrene, a-methylstyrene, vinylnaphthalene, vinylbenzenesulfonic acid, hydroxystyrene, methoxystyrene, aminostyrene, cyanostyrene, acetylstyrene, monochlorostyrene, dichlorostyrene and other halostyrenes, acrylic acid and salts, methacrylic acid and salts, methyl methacrylate, ethyl acrylate, hexyl acrylate, lauryl methacrylate, phenyl acrylate, allyl acrylate, acrylonitrile, methacrylonitrile acrylamide, methacrylamide, acrylanilide, acrylic anhydride, ethyl a-chloroacrylate, ethy maleate, maleic anhydride, polyglycol maleate, diallyl fumarate, vinyl acetate, vinyl propionate, vinyl butyrate, vinyl benzoate, vinyl chloride, vinyl bromide, vinylidene chloride, vinylidene bromide, vinylidene cyanide, vinyl methyl ketone, methyl isopropenyl ketone, vinyl carbazole, vinyl ethyl ether, isobutylene, 1,3-butadiene, isoprene, and the like.

The details of the present invention will be apparent to those skilled in the art from a consideration of the following specific examples of preferred embodiments thereof. The parts are by weight, unless otherwise specifically stated.

EXAMPLE 1

276 parts (1.5 moles) undecylenic acid, 148 parts (1.0 mole) sodium isethionate and three parts aluminum sulfate ($Al_2(SO_4)_3.14H_2O$) are charged into a kettle equipped with agitation and a Dean-Stark moisture separator. The slurry is heated in a nitrogen atmosphere. At about 180° C., a homogeneous solution results and heating is continued to 230° C. After about 1½-2 hours, no more water distills into the Dean-Stark trap. The batch is cooled to room temperature and recrystallized from a blend of 10 parts acetone/one part water. The recrystallized powder contains 5½% undecylenic acid and 94.5% of the sodium salt of undecylenic isethionate with a 98% purity based on unsaturation.

EXAMPLE 2

180 parts (1.0 mole) of 70% aqueous isethionic acid, 184 (1.0 mole) parts undecylenic acid and 200 parts benzene are heated at 75°-80° C. in a kettle equipped with Dean-Stark moisture separator and reflux condensor. Water collects in the Dean-Stark trap and is removed while the benzene is returned to the reaction mixture. After about 8½ hours, no more water was formed. The solvent is removed in vacuum leaving 292 parts of a reddish, viscous liquid which contains 1.8% undecylenic acid, balance undecenoyl isethionic acid, 97% purity.

EXAMPLE 3

Example 1 was repeated using 222 parts cinnamic acid in place of the undecylenic acid. The sodium salt of cinnamic acid isethionate was obtained by recrystallization from 10 parts acetone/one part water.

EXAMPLE 4

Example 2 was repeated using 148 parts cinnamic acid in place of undecylenic acid. Vacuum stripping produced 256 parts of a dark red cinnamoyl isethionic acid.

EXAMPLE 5

In a series of experiments tabulated below, the ester products were obtained, in the form of crystalline sodium salts, using the following procedure:

One mole (the parts by weight tabulated in Table I) of the alkenoic acid, used as a reactant, was added slowly at 10°-20° C. and while stirring to a solution of ⅓ mole (54 parts) of sodium ethylate ($NaOC_2H_5.2C_2H_5OH$) in 400 parts methanol. The reaction proceeded as illustrated in Equation 1 with the sodium salts of the alkenoic acid used precipitating so that there was obtained a paste or slurry thereof in methanol. To this paste or slurry there was then added one mole (parts by weight tabulated in Table I) of the sultone used as a reactant and this mixture was heated, with stirring, at 40°-50° C. for about one hour. The reaction proceeded as illustrated in Equation 2. The ester products were then recovered as crystalline sodium salts by centrifuging and decanting the methanol layer and drying in a vacuum oven.

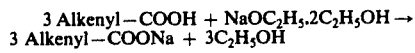

Eq. 1)

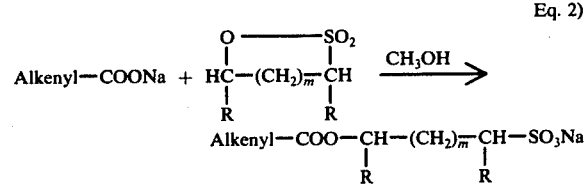

Eq. 2)

TABLE I

| Experiment | A | B | C | D | E | F | G | H | I | J | K | L | M | N |
|---|---|---|---|---|---|---|---|---|---|---|---|---|---|---|
| Reactant used | Parts by weight of reactant used ||||||||||||||
| UNDECYLENIC ACID | 184 | 184 | 184 | 184 | 184 | 184 | 184 | | | | | | | |
| CINNAMIC ACID | | | | | | | | 148 | 148 | 148 | 148 | 148 | 148 | 148 |
| 1,3-propane sultone | 122 | | | | | | | 122 | | | | | | |
| 1,3-butane sultone | | 136 | | | | | | | 136 | | | | | |
| 1,4-butane sultone | | | 136 | | | | | | | 136 | | | | |
| 1,3-pentane sultone | | | | 150 | | | | | | | 150 | | | |
| 1,4-pentane sultone | | | | | 150 | | | | | | | 150 | | |
| 1,3-hexane sultone | | | | | | 164 | | | | | | | 164 | |
| 1,4-hexane sultone | | | | | | | 164 | | | | | | | 164 |

EXAMPLE 6

To a stirred one liter reactor equipped with a condenser and two additional funnels is added 350 gms of deionized water. The vessel is heated to 80° C. To the reactor 40 gms of a mixture of vinyl acetate (320 gms) and butyl acrylate (80 gms) is added. This is followed by the addition of 0.96 gms of potassium persulfate in 50 ml of deionized water and 5.0 ml of a solution of 2.0 gms of the undecenyl isethionate sodium salt in 50 ml water. The reaction is allowed to proceed at gentle reflux. The remainder of the monomer mixture and the remainder of the undecenyl isethionate solution are gradually added from separate addition funnels. The monomer mixture is added over about 2 hours at a rate sufficient to just maintain gentle reflux at 74°-75° C. The solution of the undecenyl isethionate sodium salt is added at a rate so that all has been added when 40 gms of the monomer mixture remain. When all of the monomer is added, the kettle is heated to 85° C. for 1/2 hour. A stable latex is produced having 49.1% solids; a surface tension of 51 dynes/cm and a viscosity of 360 cps (Brookfield Spindle No. 3, 60 RPM.) Less than 2.0 gms of coagulum was collected through a 100 mesh screen.

EXAMPLE 7

To a mixture of 10.4 gm of styrene, 2.64 gm of cinamyl isethionate sodium salt in 200 gm of 75% aqueous acetone were added in three equal portions 0.12 gm of isopropyl percarbonate, added at two hour intervals. The reaction mixture was held at 60° C and agitated continuously. Total reaction time was 7 hours. The product was isolated by freeze drying. The powdery product formed was washed repeatedly with a 80/20 ethanol/water mixture and dried in vacuum oven to yield 8.3 gm of polymer. The product analyzed for 6.5% sulfur-theoretical was 9.6. The product is water dispersable and is a good emulsifier for styrene monomer in water.

EXAMPLE 8

A solution of 40 gms of styrene, 45 gm of butyl methacrylate, 13 gms of hydroxyethyl methacrylate and 3.0 gm of cinamyl isethionic acid in 300 gm of benzene was heated to 60° C in a one liter reaction vessel under nitrogen purge and 0.20 gms of isopropyl percarbonate, was added. The vessel was agitated and the reaction maintained at 60° C with cooling as required for 6 hours while three equal portions of 0.15 gm each of isopropyl percarbonate were added at two hour intervals, after the final addition of catalyst the solution held for an additional 2 hours at 60° C. A film was drawn down on a glass slide and placed in a circulating air oven at 150° C for one half hour. The resulting polymer film had good scratch resistance would not redissolve in benzene and had excellent adhesion to glass.

EXAMPLE 9

To a one liter reactor equipped with an agitator, thermometer, condenser and two gradual addition funnels are added under nitrogen purge 684.4 gm of deionized water. A pre-emulsion is prepared by mixing 128 gm of styrene, 128 gm of butyl methacrylate 48 gm of hydroxyethyl methacrylate, 16 gm of methacrylic acid, 80.0 gm of deionized water containing 6.4 gms of undecenyl isethionate sodium salt. The emulsion is prepared by high speed agitation. Meanwhile, 0.77 gm of $NaHSO_3$ is dissolved in 35.6 gm $H_2O$ is prepared and added to one of the addition funnels. The reactor is heated to 60° C and one fourth of the pre-emulsion 100 gm is added followed by 0.77 gm of $K_2S_2O_8$ and 3.6 ml of the $NaHSO_3$ solution. The reaction is allowed to exotherm and the remainder of the pre-emulsion added at 70°–75° C. at a rate to complete addition in 3 hours. The $NaHSO_3$ solution is added as required to maintain the exotherm. At the end of the addition period, any remaining $NaHSO_3$ is added and the reaction heated to 85° C and maintained for 1 hour. The reaction is cooled and neutralized with ammonia to a pH of 6–7. Films cast on a glass latern slide and dried in a circulating air oven for 1/2 hour at 150° C exhibit outstanding water resistance, especially when compared with the same recipe using an equivalent amount of a conventional emulsifier such as sodium lauryl sulfate.

We claim:

1. In an aqueous emulsion polymerization process wherein an ethylenically unsaturated monomer is copolymerized in an aqueous emulsion containing a copolymerizable surfactant as a stabilizer for the thus obtained latex; the improvement which comprises, employing as said copolymerizable surfactant an ester of undecylenic acid with a hydroxyalkane sulfonic acid, said ester having the formula:

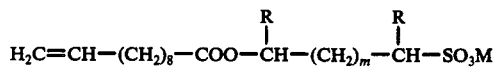

wherein:

R represents a member of the group consisting of hydrogen, methyl and ethyl;

M represents a cation selected from the group consisting of hydrogen, alkali metal, alkaline earth metal, ammonium and amino; and m represents an integer of from 0 to 4, provided however that the total number of carbon atoms in the group:

 is from 2 to about 6.

2. The copolymer, produced by the process defined in claim 1, of a polymerizable ethylenically unsaturated monomer and a copolymerizable surfactant ester of undecylenic acid with a hydroxyalkane sulfonic acid, as defined in claim 1.

3. The aqueous emulsion polymerization process defined in claim 13 wherein the copolymerizable surfactant specified is the ester of undecylenic acid with isethionic acid or a salt thereof, said ester having the formula:

wherein:

M represents a cation selected from the group consisting of hydrogen, alkali metal, alkaline earth metal, ammonium and amino.

4. The copolymer, produced by the process defined in claim 3, of a polymerizable ethylenically unsaturated monomer and a copolymerizable surfactant ester of undecylenic acid with isethionic acid, as defined in claim 3.

* * * * *

UNITED STATES PATENT AND TRADEMARK OFFICE
CERTIFICATE OF CORRECTION

PATENT NO. : 4,049,608

DATED : Sept. 20, 1977

INVENTOR(S) : Robert Steckler, Fred Robinson & Robert F. Farmer III

It is certified that error appears in the above–identified patent and that said Letters Patent are hereby corrected as shown below:

Claim 3, line 2 (col. 8, line 40): "Claim 13" should read -- claim 1 --.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*